United States Patent [19]

Rohmfeld

[11] 4,153,842

[45] May 8, 1979

[54] X-RAY DIAGNOSIS APPARATUS FOR TRANSVERSE LAYER IMAGES

[75] Inventor: Josef Rohmfeld, Erlangen, Fed. Rep. of Germany

[73] Assignee: Siemens Aktiengesellschaft, Berlin & Munich, Fed. Rep. of Germany

[21] Appl. No.: 885,492

[22] Filed: Mar. 13, 1978

[30] Foreign Application Priority Data

May 24, 1977 [DE] Fed. Rep. of Germany ....... 2723462

[51] Int. Cl.² .............................................. G03B 41/16
[52] U.S. Cl. .................................. 250/445 T; 250/360
[58] Field of Search ............................ 250/445 T, 360

[56] References Cited

U.S. PATENT DOCUMENTS 4,031,395   6/1977   Le May .............................. 250/445 T

Primary Examiner—Craig E. Church
Attorney, Agent, or Firm—Hill, Gross, Simpson, Van Santen, Steadman, Chiara & Simpson

[57] ABSTRACT

In the illustrated embodiment, each detector is reciprocally mounted for movement from a retracted position clear of the X-ray beam into an operative position. For a fan-shaped X-ray beam which is shifted by activating successive electron sources arranged about a ring anode, successive sets of detectors are activated, always on the opposite side of the patient location from the active focus. As a specific example, successive sets of electromagnets may be activated by an electronic stepping circuit to provide one-degree shifts in the active set of detectors.

2 Claims, 4 Drawing Figures

X-RAY DIAGNOSIS APPARATUS FOR TRANSVERSE LAYER IMAGES

BACKGROUND OF THE INVENTION

The invention relates to an x-ray diagnostic apparatus for producing transverse layer images of radiography subject, comprising an x-ray measuring arrangement containing an x-ray source which produces an x-ray beam penetrating the radiographic subject, the cross-sectional extent of this x-ray beam, perpendicular to the layer plane, being equal to the layer thickness, as well as containing a radiation receiver which determines the radiation intensity behind the subject, comprising means for changing the direction of the symmetry axis of the x-ray beam, and comprising a computer for transforming the signals supplied by the radiation receiver into a tomographic image, wherein the x-ray source is constructed in the form of a ring (or annulus) with an annular anode arrangement, wherein there is disposed in operative association with the anode arrangement a number of cathodes which number is dependent upon the desired measured value number, wherein, in order to change the direction of the symmetry axis of the x-ray beam, means are provided for the stepwise switching on of the electron radiation between at least one cathode in each instance and the anode arrangement, and wherein the radiation receiver, which is likewise ring-shaped, and into the opening of which a support with the radiographic subject fits, is coaxially encompassed by the x-ray source, and consists of a row of individual detectors.

The U.S. Pat. No. 3,778,614 illustrate an x-ray diagnostic apparatus for producing transverse layer images of a radiographic subject comprising an x-ray measuring arrangement containing an x-ray source which produces an x-ray beam penetrating the radiographic subject, and whose cross-sectional extent, perpendicular to the layer plane, is equal to the layer thickness, as well as containing a radiation receiver which determines the radiation intensity behind the subject, wherein the radiation source and the radiation receiver are commonly laterally adjustable and rotatably mounted. During the scanning of the radiographic subject, lateral adjustment movements and rotational movements through a predetermined angle, for example 1°, follow one another in alternate succession until a scan cycle has been completed. From the measured absorption values, a computer computes the transverse layer image in the form of a matrix of image-point-information (or data). In the case of this x-ray diagnostic apparatus, the time required for the radiographic exposure is comparatively long on account of the necessary mechanical movement of the radiation receiver and the x-ray tube. Moreover, a comparatively large constructive outlay is required for mounting the measuring arrangement.

In the publication "Computerized Tomographic Scanner" of the American Science and Engineering, Inc., Publication No. ASE-3869, an x-ray diagnostic apparatus is described wherein a radiation receiver having a ring construction is provided which manifests an opening for receiving a support table with a patient, and which consists of a row of individual detectors. Within this radiation receiver, an x-ray tube is rotatably mounted about the axis of the radiation receiver. In order to examine a radiographic subject, the x-ray tube is rotated through an angle of, for example, 360° about the patient. The radiation receiver is stationary. The measured values supplied by the radiation receiver are again processed by a computer which computes the transverse layer image. The time required for a radiographic exposure and the constructional outlay is decreased as compared with the apparatus known from the U.S. Pat. No. 3,778,614, due to the radiation receiver which is stationary during a scanning cycle.

In order to further reduce the radiographic exposure time, in accordance with the initially described construction, it is also possible to construct the x-ray source in the form of a ring (or annulus) with a ring-shaped anode arrangement, wherein there is disposed opposite the anode arrangement a number of cathodes which is dependent upon the desired measured value number. If the electron radiation is switched on in a stepwise manner between at least one cathode in each instance and the anode arrangement, the direction of the symmetry axis of the x-ray beam can thereby be changed without any mechanical movement of the x-ray source. A further shortening of the radiographic exposure time is thereby rendered possible. However, the problem which arises is that the x-radiation cannot initially pass through the radiation receiver directly subsequent to issuance from the x-ray source, but that it can impinge upon the corresponding number of detectors of the radiation receiver only when it has issued from the radiographic subject.

SUMMARY OF THE INVENTION

The object underlying the invention consists in constructing an x-ray diagnostic apparatus of the type initially cited such that, during the scanning of a radiographic subject, always only those detectors of the radiation receiver lie in the x-ray beam which are required for the detection of the x-ray beam issuing from the radiographic subject.

In accordance with the invention, this object is achieved by virtue of the fact that each detector is adjustably mounted in such a manner that it can be brought, independently of the other detectors, from one position outside the x-ray beam into a position in which it is impinged upon by the x-ray beam, and that a device is present by means of which the detector adjustment proceeds in dependence upon the respective position of the symmetry axis of the x-ray beam in such a manner that the x-ray beam initially passes by the detectors and then impinges upon a corresponding number of detectors. In the inventive x-ray diagnosis apparatus, the detectors can be moved into or out of the x-ray beam entirely as desired. Thus, it is possible, in dependence upon the respective position of the symmetry axis of the x-ray beam, to always shift those particular detectors into the x-ray beam which are required for the purpose of detection subsequent to issuance of the x-ray beam from the patient.

It is particularly expedient to provide an electromagnet for each detector for the purpose of its adjustment, which electromagnet is connected to a stepping circuit. In the case of an electromagnetic detector adjustment, a very rapid scanning of the photographic subject is possible. However, within the scope of the invention, the detector adjustment can also proceed in a purely mechanical fashion, in that each detector with an adjustment element projects (or extends) into the track (or path) of a slide which circulates (or rotates) during the scanning of the radiographic subject and acts upon each detector for the purpose of adjustment of said detector in dependence upon the position of the symmetry axis of the x-ray beam.

The invention shall be explained in further detail in the following on the basis of the sample embodiment illustrated in the accompanying sheets of drawings; other objects, features and advantages will be apparent from this detailed disclosure and from the appended claims.

DETAILED DESCRIPTION

Figure 1:
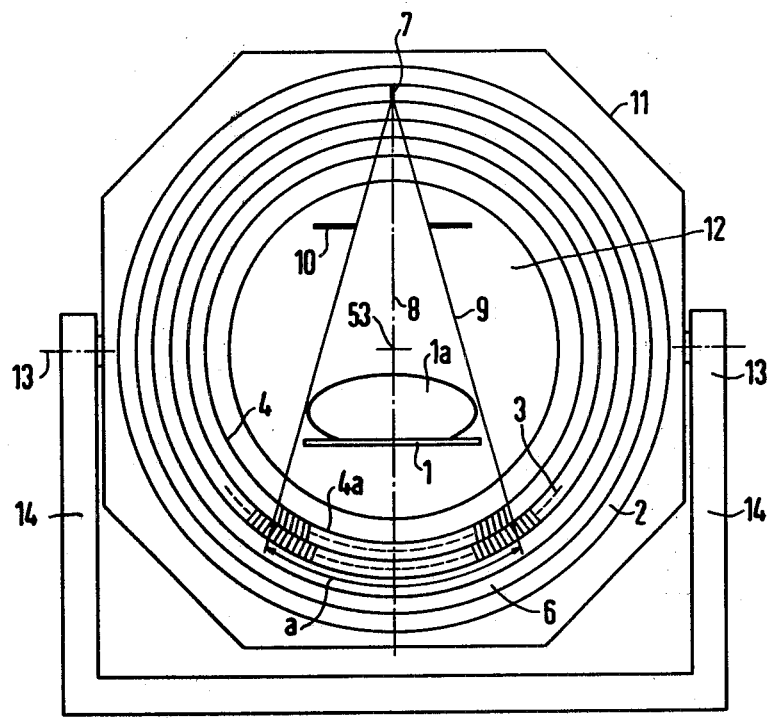
FIGS. 1 and 1a illustrate two diagrammatic views of an x-ray diagnostic apparatus for the purpose of explaining the inventive concept, and are taken transversely of and longitudinally of the patient support, respectively.
Figure 1A:
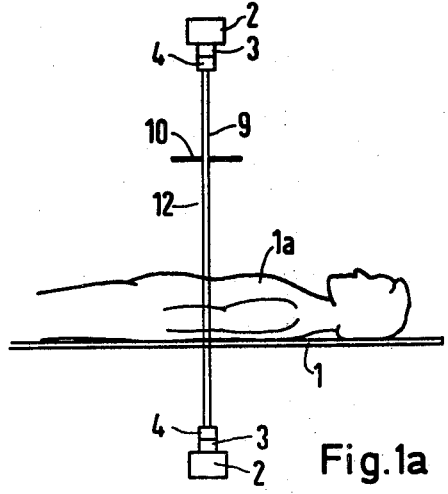

As illustrated in FIGS. 1 and 1a, the x-ray diagnosis apparatus for producing transverse layer images of a patient 1a lying on a support 1 has an x-ray measuring arrangement manifesting an x-ray source 2 constructed in the form of a ring (or annulus). X-ray source 2 has a ring-shaped (or annular) anode 5, illustrated in greater detail in FIG. 2, and opposite said anode, it has a number of cathodes which is dependent upon the desired measured value number. The measuring arrangement further manifests a radiation receiver 3, likewise of annular configuration, which is coaxially encompassed by the x-ray source 2, and which consists of a row of individual detectors. Within the ring-shaped radiation receiver 3, there is disposed a collimator ring 4, which exhibits a sector 4a with collimator lamellae (or blades), which is constructed such that the collimator lamellae are aligned (or oriented) to the respective focus lying on the anode 5 of x-ray source 2. In FIG. 1, a central axis 53 is additionally illustrated for components 2, 3, 4, which runs parallel to the longitudinal direction of the support 1.

For an examination of patient 1a, the focus, for which a position 7 is illustrated in FIG. 1, is advanced electronically in a stepwise fashion through, for example, one angular degree at a time until it has covered a range of 360°. The symmetry axis 8 of x-ray beam 9, which is fan-shaped in the example, thus likewise covers (or sweeps over) this range. By means of a schematically illustrated collimator 10, x-ray beam 9 is diaphrammed-in such that its extent (or spread) in the layer plane of the examined patient 1a is of such a magnitude that the entire layer is simultaneously penetrated by radiation, and that its extent perpendicular to this layer plane is equal to the layer thickness. The collimator 10 also travels in accordance with the stepwise movement of x-ray beam 9. To this end, collimator ring 4 is correspondingly rotated about central axis 53.

In FIG. 1, an additional housing 11 is illustrated in which the components of the x-ray diagnostic apparatus are housed. The housing 11 has an opening 12 into which the support 1 with patient 1a fits. It is pivotally mounted about a horizontal axis 13 on two supports 14 such that the examined body layer of patient 1a can also run obliquely through the body.

Figure 2:
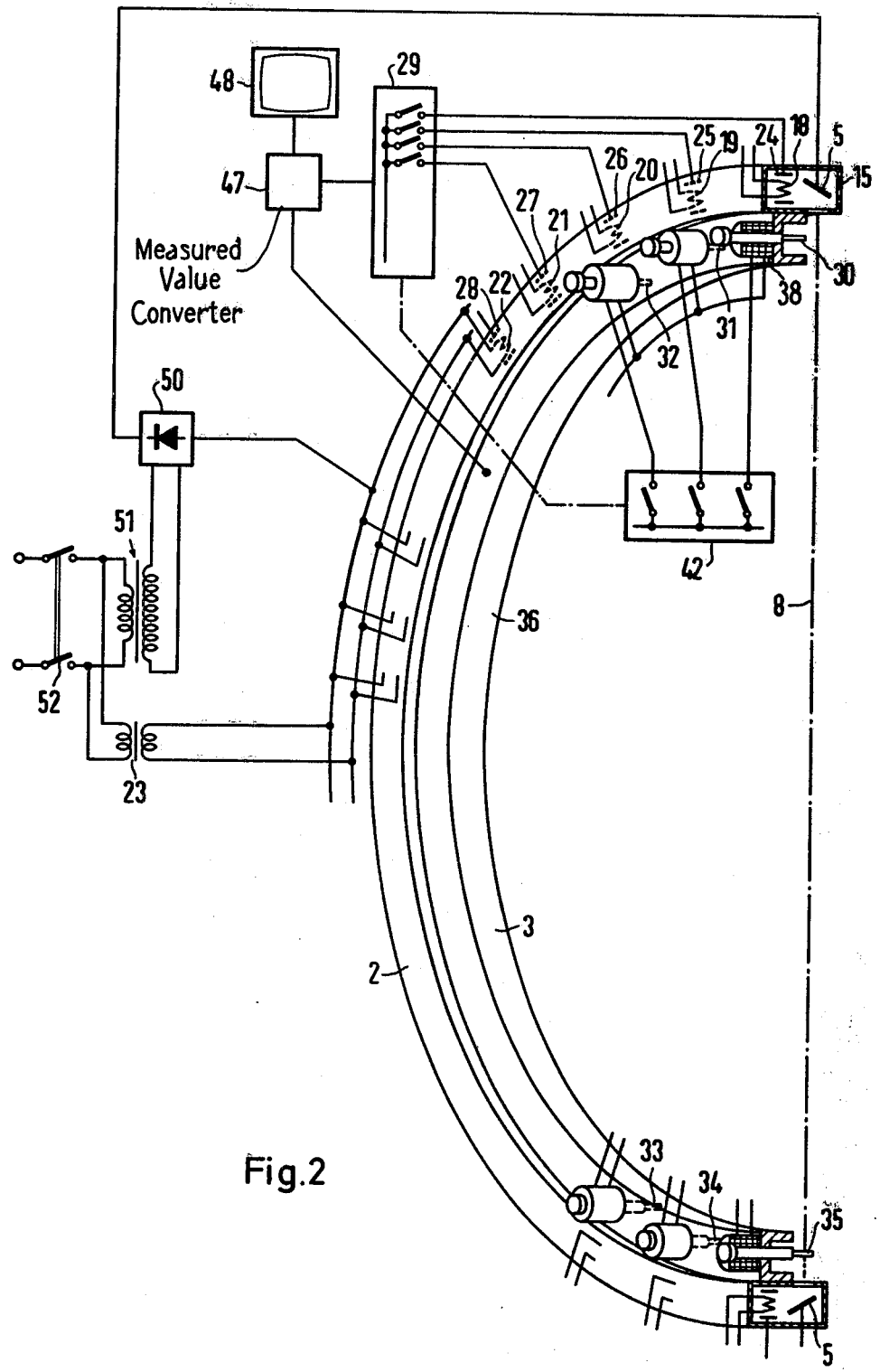
FIG. 2 illustrates a diagrammatic view of a radiographic system embodying the apparatus of FIGS. 1 and 1a, and indicating pertinent parts of the apparatus on a larger scale and partly in section.

From FIG. 2, the construction of x-ray source 2 and radiation receiver 3 is clearly apparent. The x-ray source 2 has a ring-shaped (or annular) tube 15 in which anode 5, which is likewise ring-shaped, is disposed. Opposite anode 5 there are arranged a number of cathodes such as indicated at 18 through 22 which are commonly connected to a filament transformer 23. In order to control (or operate) the electron radiation between cathodes 18 through 22, etc. and anode 5, each cathode 18 through 22, etc., is associated with one control grid 24 through 28, etc., respectively. The control grids 24 through 28, etc., are connected to a control device 29. In FIG. 2, the spatial intervals between the cathodes are not illustrated true to scale.

Figure 3:
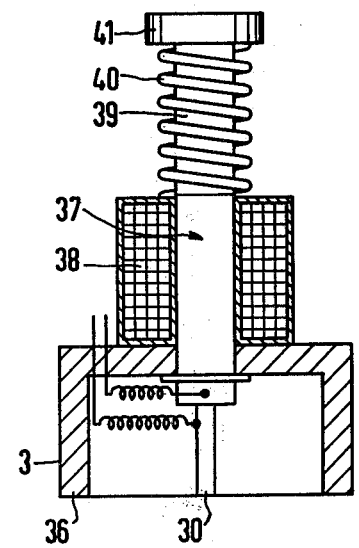
FIG. 3 (on sheet one of the drawings) is an enlarged somewhat diagrammatic sectional view illustrating a detector of the radiation receiver of the apparatus according to FIGS. 1 and 2 with its adjustment device.

Radiation receiver 3 consists of a row of individual detectors 30 through 35, etc. The detectors 30 through 35, etc., are arranged in a housing 36 which shields (or screens, or blocks off) x-rays, and said detectors are connected to a measured value converter 47. From the signals supplied by detectors 30 through 35, etc., during a scanning of patient 1a, converter 47 generates an image of the irradiated transverse layer and effects its reproduction on a TV display unit 48. In FIG. 3, the connection of detectors 30 through 35, etc., to the housing 36 is illustrated using detector 30 as an example. The detector is mounted on a square cross section bolt 37 which is surrounded by a coil 38 to form an electromagnet. The square-sectioned bolt, in its part 39 projecting at the top beyond coil 38 in FIG. 3 consists of a soft magnetic material. There is mounted in encircling relation to magnetic part 39, a compression spring 40 which is supported against a flange or head 41 of the square bolt 37 and against coil 38. In the retracted positions as illustrated in FIG. 3, the detectors such as 30 are disposed in housing 36; thus, they are not impinged upon by x-radiation. They are movable into the beam of x-radiation—of which FIG. 2 illustrates, for example, a position of the symmetry axis 8—if the associated coil, for example coil 38, is excited. In this case, the coil 38, draws magnetic part 39, FIG. 3, of square bolt 7 into its interior, whereby the spring 40 is compressed. The detector is thus shifted out of housing 36 into x-ray beam 9, as is illustrated in the lower part of FIG. 2 in connection with detector 35. The switching on of the coils 38 proceeds by means of a stepping switch device 42 which is synchronized with the switching on of the x-radiation; i.e., the actuation of grids 24 through 28, etc.

In order to examine the patient 1a, converter 47 effects the stepwise switching on of the electron radiation between cathodes 18 through 22, etc. and anode 5 via the control device 29. By way of example, first the electron radiation of cathode 18, then of cathode 19, then of cathode 20, etc., is switched on. The arrangement of cathodes can be effected such that the x-ray beam travels through one angular degree at a time; namely, as often as is necessary until a total angle of 360° has been covered. Those detectors which are disposed at the side of issuance of the x-ray beam 9 from x-ray source 2 thus lie in housing 36; i.e., their coils 38 are not excited. On the contrary, the coils 38 of those detectors are excited which detect the x-radiation issuing from patient 1a. In FIG. 1, the latter are those detectors which lie within section "a" of x-ray beam 9. During the travel (or migration) of x-ray beam 9; i.e., during the stepwise advancement of symmetry axis 8, the detectors are also correspondingly moved. It is thereby guaranteed that the x-radiation issuing from radiation source 2 can travel in an unimpeded fashion past the detectors of radiation receiver 3 and that said x-radiation only then impinges upon the latter detectors after it has passed through patient 1a.

FIG. 2 additionally illustrates the fact that the supply of the x-ray source 2 proceeds by means of a high voltage rectifier 50 which is connected to the secondary winding of a high voltage transformer 51. The high voltage transformer 51 and the filament transformer 23 are capable of being connected to the mains supply via a main switch 52.

Within the scope of the invention, it is also conceivable to adjust detectors 30 through 35, etc., not electromagnetically via the stepping switch device 42, but in a purely mechanical fashion via a control cam plate (or disk) or a control slide. This cam plate, or the control slide, respectively, may, for example, be connected to the collimator ring 4 and, pursuant to rotation of the collimator ring 4, may act upon the spring-loaded reciprocally mounted tappets connected with the detectors 30 through 35, etc., such that the detectors required in each instance are moved into the x-ray beam 9.

It will be apparent that many modifications and variations may be effected without departing from the scope of the novel concepts and teachings of the present invention.

I claim as my invention:

1. An x-ray diagnostic apparatus for producing transverse layer images of a radiographic subject, comprising an x-ray measuring arrangement including an x-ray source for producing an x-ray beam penetrating a transverse layer region of a radiographic subject with the beam having a cross-sectional extent perpendicular to the plane of the layer region generally equal to the layer thickness, and a radiation receiver for determining the radiation intensity issuing from the layer region; a convertor connected to the radiation receiver for transforming the signals delivered by the radiation receiver into a tomographic image; the x-ray source comprising a ring-shaped anode arrangement, and a series of cathodes being arranged opposite the anode arrangement; and beam shifting means for changing the direction of the symmetry axis of the x-ray beam comprising means for the stepwise switching on of electron radiation between at least one cathode in each instance and the anode arrangement; the radiation receiver being of a ring configuration for surrounding the layer region and being disposed radially inwardly relative to the x-ray source, and comprising a series of individual detectors; characterized in each detector (30 through 35, etc.) being adjustably mounted such that it can be brought, independently of the other detectors, from a position clear of the x-ray beam (9) into a position in which it is impinged upon by the x-ray beam (9), and a device (37 through 42) being coupled with said detectors for effecting the detector adjustment in dependence upon the respective position of the symmetry axis (8) of the x-ray beam (9) such that the x-ray beam (9) initially passes by the detectors (30 through 35, etc.), and then impinges upon a corresponding selectable number of detectors (30 through 35, etc.).

2. Apparatus according to claim 1, characterized in the device (37 through 42) for the detector adjustment comprising one electromagnet (35) for each detector (30 through 35, etc.), and further comprising a stepping circuit (42) for selectively actuating the electromagnets (35).

* * * * *